United States Patent [19]
Kamohara et al.

[11] Patent Number: 5,907,002
[45] Date of Patent: May 25, 1999

[54] DENTAL IMPRESSION SILICONE COMPOSITION

[75] Inventors: Hiroshi Kamohara; Nobuyuki Hattori; Makiko Komoto, all of Tokyo, Japan

[73] Assignee: GC Corporation, Tokyo, Japan

[21] Appl. No.: 08/879,190

[22] Filed: Jun. 20, 1997

[30] Foreign Application Priority Data

Jul. 3, 1996 [JP] Japan .................................. 8-191643

[51] Int. Cl.$^6$ ................................ A61K 6/10; C08K 3/02
[52] U.S. Cl. ........................ 523/109; 524/435; 524/493; 524/506; 524/731; 524/862; 528/31; 528/32; 106/35
[58] Field of Search ............................ 523/109; 524/506, 524/435, 493, 731, 862; 528/31, 32

[56] References Cited

U.S. PATENT DOCUMENTS

| | | | |
|---|---|---|---|
| 3,775,452 | 11/1973 | Karstedt ..................................... | 528/15 |
| 4,035,453 | 7/1977 | Hittmair et al. ........................ | 524/862 |
| 4,550,030 | 10/1985 | Ohi et al. . | |
| 4,604,142 | 8/1986 | Kamohara et al. . | |
| 4,720,521 | 1/1988 | Spielvogel et al. ........................ | 528/31 |
| 4,741,855 | 5/1988 | Grote et al. ............................. | 252/173 |
| 4,778,832 | 10/1988 | Futami et al. ........................... | 523/109 |
| 4,814,011 | 3/1989 | Kamohara et al. . | |
| 4,909,847 | 3/1990 | Ohi et al. . | |
| 4,911,759 | 3/1990 | Ohi et al. . | |
| 4,965,295 | 10/1990 | Schwabe et al. ........................ | 523/109 |
| 5,064,891 | 11/1991 | Fujiki et al. ............................. | 523/109 |
| 5,203,914 | 4/1993 | Futami et al. . | |
| 5,543,443 | 8/1996 | Rajaiah et al. ............................ | 528/31 |
| 5,631,320 | 5/1997 | Kamohara et al. . | |
| 5,637,628 | 6/1997 | Kamohara et al. . | |

*Primary Examiner*—Andrew E. C. Merriam
*Attorney, Agent, or Firm*—Oblon, Spivak, McClelland, Maier & Neustadt, P.C.

[57] ABSTRACT

A dental impression silicone composition comprising: (A) 100 parts by weight of an organopolysiloxane having at least two aliphatic unsaturated hydrocarbons in one molecule; (B) from 0.1 to 30 parts by weight of an organohydrogen polysiloxane having at least three hydrogen atoms directly bonded to the silicon atom in one molecule; (C) from 10 to 500 ppm, based on the total amount of the components (A) and (B), of a silicone-soluble platinum compound; (D) from 10 to 500 parts by weight of an inorganic filler; (E) from 5 to 50 parts by weight of a fine silica powder having a BET specific surface area of from 50 to 500 m$^2$/g, whose surface is made hydrophobic; (F) from 0.5 to 50 parts by weight of a nonionic surfactant; and (G) from 10 to 200 parts by weight of a methylphenyl polysiloxane, being disclosed, the invention providing a dental impression silicone composition used for the preparation of oral models that are required in the preparation of dental prostheses in the dentistry, such as crowns, inlays, and dentures, soft in the hardness after setting, large in the strain in compression, good in the wettability against the water content such as saliva, and being so large in the tear strength that the set material hardly comes off.

6 Claims, No Drawings

DENTAL IMPRESSION SILICONE COMPOSITION

FIELD OF THE INVENTION

The present invention relates to a mold-taking material which is used for the preparation of oral models that are required in the preparation of dental prostheses in the dentistry, such as crowns, inlays, and dentures (the mold-taking material being hereinafter referred to as "impression material") and in particular, to a dental impression silicone composition to be used for precision impression.

BACKGROUND OF THE INVENTION

As dental elastic impression materials, those in which the stock is comprised of agar hydrocolloid, alginates, polysulfide rubbers, polyether rubbers, silicone rubbers, or the like are used. These elastic impression materials are suitable for impression taking of complicated forms having an undercut in the oral cavity, such as tooth roots, dentitions, jaws, and mucous membranes because the deformation generated upon being removed out from the oral cavity is quickly recovered.

Among these elastic impression materials, the agar hydrocolloid impression materials and the alginate impression materials have a suitable elasticity from the clinical viewpoints. On the other hand, however, these elastic materials are large in the permanent deformation having a high content of water in the structures thereof, and therefore, they have such properties that the water content is vaporized from the taken impressions, resulting in big changes in the dimension with a lapse of time. Furthermore, since these elastic materials have such drawbacks that they are likely to come off due to their low tear strengths, they are mainly used for preliminary impression taking.

On the other hand, the synthetic rubber-based elastic impression materials in which the stock is comprised of polysulfide rubbers, polyether rubbers, silicone rubbers, or the like have such advantages that the detail reproducibility is superior, the changes in the dimension are extremely small, and they hardly come off. For these reasons, these synthetic rubber-based elastic impression materials are mainly used for precision impression taking. However, the polysulfide-based impression materials in which the stock is comprised of polysulfide rubbers have such drawbacks that the unpleasant odor is strong and that the setting is slow. Also, the polyether rubber-based impression materials are superior in the hydrophilicity and convenient for taking impressions in the state that a saliva is present as in the oral cavity. However, the polyether rubbers-based impression materials have such a drawback that it involves difficulty to remove out the impression from the oral cavity of a patient, because the rubber elasticity is low, and the set material is hard. Furthermore, since the polyether rubbers have an inherent bitter taste, the polyether rubber-based impression materials have such a drawback that they give an unpleasant feeling to a patient. Moreover, since the polyether rubber-based impression materials have a large permanent deformation, there is a danger that the deformation occurs at the time of removing out the impression from the oral cavity.

In contrast thereto, the impression materials in which the stock is comprised of silicone rubbers include a condensation polymerization type and an addition polymerization type depending on the setting process thereof. Any of these room temperature-vulcanizing silicone rubbers are used as dental silicone impression materials. Of these materials, the addition polymerization type silicone impression materials are sharp in the setting, small in the permanent deformation and extremely small in the dimensional changes and hence, are most likely used as the precision impression. However, as compared with the alginate impression materials, the silicone rubber-based impression materials are so high in the hardness after the setting that when the impression is removed out from the oral cavity of a patient, they give the patient pain, and when a plaster model is prepared using the thus taken impression and then removed out from the impression, the plaster may sometimes be broken depending on the site. Also, as compared with the polyether rubber-based impression materials, the silicone rubber-based impression materials are inferior in the hydrophilicity that the detail impression may be unclear due to the saliva in the oral cavity. In addition, since the tear strength is not sufficiently high, when the impression is removed out from the oral cavity of a patient, the impression material may come off depending on the impression site, resulting in making the impression incomplete.

In the light of the above, while the currently used impression materials have inherent advantages, they involve various disadvantages. Any of these impression materials were incomplete as impression materials for reproducing the state in the oral cavity in detail and preparing dental prostheses with a good fitness accuracy, without giving a patient pain.

Of the above-described respective impression materials, the present inventors paid attention to the addition polymerization type silicone impression materials which are not only small in the dimensional changes and permanent deformation but also superior in obtaining that an accurate impression can be taken. Thus, an object of the present invention is to develop a dental impression silicone composition provided with excellent properties for the precision impression by improving such defects of the addition polymerization type silicone that the hardness after the setting is so high that the strain in compression is small, the wetting against the water content such as saliva is poor and that the tear strength is not sufficient, while enhancing the superior characteristics thereof.

SUMMARY OF THE INVENTION

The inventors made extensive investigations in order to attain the above-described object of the present invention. As a result, success has been achieved in obtaining a dental impression silicone composition which is large in the strain in compression, is small in the permanent deformation and is rich in the elasticity, neither generates sags nor comes off at the time of impression taking, and is superior in the wettability against water, by adding specific amounts of a specific fine silica powder, a nonionic surfactant and a methylphenyl polysiloxane to an addition polymerization type silicone impression material comprising an organopolysiloxane having at least two aliphatic unsaturated hydrocarbons in one molecule, an organohydrogen polysiloxane having at least three hydrogen atoms directly bonded to the silicon atom in one molecule, a silicone-soluble platinum compound, and an inorganic filler, thus leading to the accomplishment of the present invention.

That is, the dental impression silicone composition according to the present invention comprises the following components (A) to (G):

(A) 100 parts by weight of an organopolysiloxane having at least two aliphatic unsaturated hydrocarbons in one molecule;

(B) from 0.1 to 30 parts by weight of an organohydrogen polysiloxane having at least three hydrogen atoms directly bonded to the silicon atom in one molecule;

(C) from 10 to 500 ppm, based on the total amount of the components (A) and (B), of a silicone-soluble platinum compound;

(D) from 10 to 500 parts by weight of an inorganic filler;

(E) from 5 to 50 parts by weight of a fine silica powder having a BET specific surface area of from 50 to 500 $m^2/g$, whose surface is made hydrophobic;

(F) from 0.5 to 50 parts by weight of a nonionic surfactant; and (G) from 10 to 200 parts by weight of a methylphenyl polysiloxane.

DETAILED DESCRIPTION OF THE INVENTION

In the dental impression silicone composition comprising the components (A) to (G) according to the present invention, the component (A) is an organopolysiloxane having at least two aliphatic unsaturated hydrocarbons in one molecule. As this organopolysiloxane, those which are linear and are terminated by vinylsilyl groups at the both ends of the molecular chain thereof are preferred. In this case, the end vinyl group may be in the plural number, and the vinyl group may be contained in the chain.

The organohydrogen polysiloxane as the component (B) has at least three hydrogen atoms directly bonded to the silicon atom in one molecule and acts as a crosslinking agent. In the case where the amount of the organohydrogen polysiloxane added is less than 0.1 part by weight based on 100 parts by weight of the component (A), not only the hardness of the set material is lowered, the setting rate is slow; and in the case where the amount of the organohydrogen polysiloxane added exceeds 30 parts by weight based on 100 parts by weight of the component (A), the set material is very brittle. Accordingly, the both cases are not preferred.

The silicone-soluble platinum compound as the component (C) acts as an addition reaction catalyst, and known chloroplatinate, alcohol-modified chloroplatinates, and complexes of chloroplatinate with olefins can be used. In particular, a chloroplatinate-vinylsiloxane complex is suitably used. The addition amount of the silicone-soluble platinum compound is in the range of from 10 to 500 ppm based on the total amount of the components (A) and (B). In the case where the addition amount of the component (C) is less than 10 ppm, the setting rate is slow, and if substances inhibiting the catalytic activity of the platinum compound are present in trace amounts, there is such a problem that the setting is slow. Also, in the addition of the component (C) exceeds 500 ppm, the setting rate is too high and the production cost is high, leading to economical disadvantages. Preferably, the silicone-soluble platinum compound such as chloroplatinate is used upon being dissolved in alcohol-based, ketone-based, ether-based, or hydrocarbon-based solvents, or polysiloxane oils.

The inorganic filler as the component (D), quartz, cristobalite, diatomaceous earth, fused quartz, glass fibers, titanium dioxide, and fumed silica can be used. The amount of the inorganic filler added is from 10 to 500 parts by weight based on 100 parts by weight of the component (A). In the case where the addition amount of the component (D) is less than 10 parts by weight, the set material is brittle; and in the case where the addition amount of the component (D) exceeds 500 parts by weight, the viscosity is too high so that the resistance at the time of kneading is excessively high, whereby the resulting material is no longer suitable as the dental impression material.

The fine silica powder used as the component (E) has a BET specific surface area of from 50 to 500 $m^2/g$, and its surface is made hydrophobic. This hydrophobic fine silica powder is substantially obtained by the heat treatment of, e.g., fumed silica as a hydrophilic silica with a surface treatment agent such as methyltrichlorosilane, dimethyldichlorosilane, trimethylchlorosilane, corresponding alkoxysilanes, octamethylcyclotetrasiloxane, hexamethyldisiloxane, hexamethyldisilazane, and mixtures thereof, or with a mixture of such surface treatment agent and water. Known hydrophobic silica in which all or a major part of the silanol groups present on the surface are terminated by a hydrophobic group such as a $(CH_3)_3SiO_{1/2}$ unit, a $(CH_3)_2SiO_{2/2}$ unit, and a $CH_3SiO_{3/2}$ unit can be used. The hydrophobic fine silica powder is able to not only make the impression material kneaded mixture have a desired fluidity characteristic without increasing the hardness of the set material but also serve for improving the wettability against water by means of a mutual interaction with the components (F) and (G) as described later. Also, since the tear strength is improved, there is no fear that the impression material entered into the detail comes off at the time of removing out the impression. The hydrophobic fine silica powder must have a BET specific surface area of from 50 to 500 $m^2/g$. In the case where the BET specific surface area is less than 50 $m^2/g$, the tear strength is not sufficient so that the impression material comes off, while in the case where the BET specific surface area exceeds 500 $m^2/g$, the permanent deformation is undesirably too large. Furthermore, the amount of the hydrophobic fine silica powder compounded is from 5 to 50 parts by weight based on 100 parts by weight of the component (A). In the case where the compounding amount of the component (E) is less than 5 parts by weight, not only the tear strength is insufficient, but also bleeding of the polysiloxane oil likely occurs. On the other hand, in the case where the compounding amount of the component (E) exceeds 500 parts by weight, the viscosity of the composition is too high so that the kneading operation is difficult.

Suitable examples of the nonionic surfactant as the component (F) include nonionic surfactants having a combination of a hydrophilic group with an alkyl group as a lipophilic group, or nonionic surfactants having a combination of a hydrophilic group with a fluorocarbon group in which hydrogen atoms in an alkyl group as a lipophilic group are substituted with fluorine atoms.

The nonionic surfactants having a combination of a hydrophilic group with an alkyl group as a lipophilic group include:

(1) Ether types such as polyoxyethylene alkyl ethers, polyoxypropylene alkyl ethers, and polyoxyethylene alkylphenyl ethers, in which the addition mole number of ethylene oxide or propylene oxide is from 1 to 30, and the carbon atom number of the alkyl group is from 12 to 22;

(2) Partial ester types between a polyhydric alcohol and a fatty acid having 12 to 22 carbon atoms, such as sorbitan fatty acid esters, glycerin fatty acid esters, polyglycerin fatty acid esters, ethylene glycol fatty acid esters, polyethylene glycol fatty acid esters, propylene glycol fatty acid esters, and pentaerythritol fatty acid esters;

(3) Ether ester types such as polyoxyethylene sorbitan fatty acid esters, polyoxyethylene sorbitol fatty acid esters, polyoxyethylene mannitol fatty acid esters, polyoxyethylene glycerin fatty acid esters, and polyoxyethylene propylene glycol monomeric fatty acid esters, in which the addition mole number of ethylene oxide is from 1 to 30, and the carbon atom number of the fatty acid is from 12 to 22; and (4) Ester types having from 1 to 30 moles of ethylene oxide addition polymerized therewith, such as polyoxyethylene caster oil/hardened caster oil, polyoxyethylene lanolin derivatives, and polyoxyethylene beeswax derivatives. Examples of the nonionic surfactants having a combination of a hydrophilic group with a fluorocarbon group in which hydrogen atoms in an alkyl group as a lipophilic group are substituted with fluorine atoms include those represented by the following formulae:

$$Rf-O(C_nH_{2n}O)_nH$$

$$RfO(CH_{2n})_lO(C_nH_{2n}O)_m$$

$$RfBN(R')(C_2H_4O)_nH$$

wherein Rf represents a fluorinated aliphatic group or a fluorinated aromatic group each having from 1 to 20 carbon atom, provided that the aliphatic group may be linear, branched, or cyclic; B represents a divalent connecting group (e.g., —SO$_2$—, —CO—); R' represents a hydrogen atom or an alkyl group having from 1 to 20 carbon atoms; and l, m, and n each represents an integer of from 1 to 50.

The nonionic surfactant which is used in the present invention effectively acts for the purpose of improving the wettability against water in the co-presence of the components (E) and (G). The content of the nonionic surfactant must be in the range of from 0.5 to 50 parts by weight based on 100 parts by weight of the component (A). In the case where the content of the component (F) is less than 0.5 part by weight, the wettability against water is insufficient, while in the case where the content of the component (F) exceeds 50 parts by weight, the permanent deformation is large. These nonionic surfactants can be used alone or in admixture of two or more.

As the methylphenyl polysiloxane which is used as the component (G), those represented by the following formula can be used.

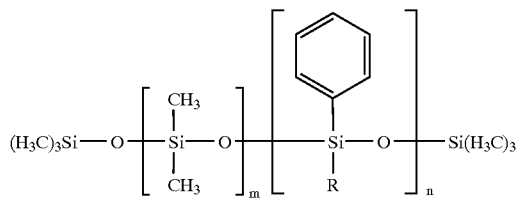

In the formula, R represents a methyl group or a phenyl group; and m and n each represents an integer, m≧0, n≧0)

The methylphenyl polysiloxane as the component (G) has effects for making the set material soft without changing the permanent deformation as well as for increasing the strain in compression. Also, the methylphenyl polysiloxane improves the wettability against water in the co-presence of the components (E) and (F). The content of the methylphenyl polysiloxane must be from 10 to 200 parts by weight based on 100 parts by weight of the component (A). In the case where the content of the component (G) is less than 10 parts by weight, the elasticity is insufficient, while in the case where the content of the component (G) exceeds 200 parts by weight, the bleeding undesirably occurs from the surface of the set material.

Moreover, in the present invention, so far as the characteristics of the composition are not lost, various inorganic or organic colorants can be used. Examples of the colorants which can be used include those used for the usual silicone impression materials, such as red oxide, titanium white, titanium yellow, and cobalt blue.

The present invention will be described in more detail with reference to the following Examples, but it should not be construed that the invention is limited thereto.

EXAMPLE 1

A base paste and a catalyst paste each having the following composition were prepared.

(Base Paste)

| | |
|---|---|
| Dimethyl polysiloxane terminated by dimethylvinylsiloxy groups at the both ends of the molecular chain: | 100 parts by weight |
| Linear methylhydrogen polysiloxane containing 40 mole % of a methylhydrogen siloxane unit: | 3 parts by weight |
| Polyoxyethylene nonylphenyl ether: | 10 parts by weight |
| Quartz: | 20 parts by weight |

(Catalyst Paste)

| | |
|---|---|
| Dimethyl polysiloxane terminated by dimethylvinylsiloxy groups at the both ends of the molecular chain: | 100 parts by weight |
| Silicone oil solution containing 0.4% by weight of 1,3-divinyltetramethyl disiloxane-platinum complex: | 3 parts by weight |
| Hydrophobic fine silica powder having a BET specific surface area of 100 m$^2$/g, whose surface is terminated by a (CH$_3$)$_3$SiO$_{1/2}$ unit: | 10 parts by weight |
| Methylphenyl polysiloxane (phenyl group content: 5 mole %): | 20 parts by weight |

Equal amounts of the base paste and catalyst paste were taken and kneaded for 30 seconds by means of a spatula, and the kneaded mixture was measured for the strain in compression and permanent deformation according to the testing process as defined in JIS (Japanese Industrial Standard) T6513. The larger the strain in compression value, the softer the set material. Also, the smaller the permanent deformation value, the sharper the setting and the smaller the deformation. The tear test was carried out based on a tear test specimen A-model in the testing process as defined in JIS K6301 after kneading the both pastes. With respect to the wettability against water, after kneading the both pastes, a disk sample having a diameter of 30 mm and a thickness of 1 mm was prepared, and a contact angle to water was measured by means of a contact angle meter. The results obtained are summarized in Table 1.

As shown in Table 1, with respect to the composition of Example 1, though the strain in compression was large, the permanent deformation was sufficiently small, the composition was sharply set, and the set material was soft and small in the deformation. Also, the tear strength was so high that the set material was confirmed to hardly come off. In addition, the contact angle to water was so small that the set material had a superior wettability against water.

EXAMPLE 2

A base paste and a catalyst paste each having the following composition were prepared.

(Base Paste)

| | |
|---|---|
| Dimethyl polysiloxane terminated by dimethylvinylsiloxy groups at the both ends of the molecular chain: | 100 parts by weight |
| Linear methylhydrogen polysiloxane containing 40 mole % of a methylhydrogen siloxane unit: | 3 parts by weight |

-continued

| | | |
|---|---|---|
| Polyoxyethylene lauryl ether: | 1 | part by weight |
| Quartz: | 800 | parts by weight |
| (Catalyst Paste) | | |
| Dimethyl polysiloxane terminated by dimethylvinylsiloxy groups at the both ends of the molecular chain: | 100 | parts by weight |
| Silicone oil solution containing 0.4% by weight of 1,3-divinyltetramethyl disiloxane-platinum complex: | 3 | parts by weight |
| Hydrophobic fine silica powder having a BET specific surface area of 100 m²/g, whose surface is terminated by a $(CH_3)_3SiO_{1/2}$ unit: | 20 | parts by weight |
| Methylphenyl polysiloxane (phenyl group content: 25 mole %): | 400 | parts by weight |
| Quartz: | 200 | parts by weight |

Equal amounts of the base paste and catalyst paste were taken and kneaded for 30 seconds by means of a spatula, and the same tests as in Example 1 were carried out. The results obtained are summarized in Table 1.

As shown in Table 1, with respect to the composition of Example 2, though the strain in compression was large, the permanent deformation was sufficiently small, the composition was sharply set, and the set material was soft and small in deformation. Also, the tear strength was so high that the set material was confirmed to hardly come off. In addition, the contact angle to water was so small that the set material had a superior wettability against water.

EXAMPLE 3

A base paste and a catalyst paste each having the following composition were prepared.

| | |
|---|---|
| (Base Paste) | |
| Dimethyl polysiloxane terminated by dimethylvinylsiloxy groups at the both ends of the molecular chain: | 100 parts by weight |
| Linear methylhydrogen polysiloxane containing 40 mole % of a methylhydrogen siloxane unit: | 3 parts by weight |
| Polyoxyethylene octylphenyl ether: | 100 parts by weight |
| Cristobalite: | 100 parts by weight |
| (Catalyst Paste) | |
| Dimethyl polysiloxane terminated by dimethylvinylsiloxy groups at the both ends of the molecular chain: | 100 parts by weight |
| Silicone oil solution containing 0.4% by weight of 1,3-divinyltetramethyl disiloxane-platinum complex: | 3 parts by weight |
| Hydrophobic fine silica powder having a BET specific surface area of 100 m²/g, whose surface is terminated by a $(CH_3)_3SiO_{1/2}$ unit: | 100 parts by weight |
| Methylphenylpolysiloxane (phenyl group content: 50 mole %): | 150 parts by weight |

Equal amounts of the base paste and catalyst paste were taken and kneaded for 30 seconds by means of a spatula, and the same tests as in Example 1 were carried out. The results obtained are summarized in Table 1.

As shown in Table 1, with respect to the composition of Example 3, though the strain in compression was large, the permanent deformation was sufficiently small, the composition was sharply set, and the set material was soft and small in the deformation. Also, the tear strength was so high that the set material was confirmed to hardly come off. In addition, the contact angle to water was so small that the set material had a Superior wettability against water.

COMPARATIVE EXAMPLE 1

A base paste and a catalyst paste each having the following composition but not containing the component (E) as in the present invention were prepared.

| | |
|---|---|
| (Base Paste) | |
| Dimethyl polysiloxane terminated by dimethylvinylsiloxy groups at the both ends of the molecular chain: | 100 parts by weight |
| Linear methylhydrogen polysiloxane containing 40 mole % of a methylhydrogen siloxane unit: | 3 parts by weight |
| Polyoxyethylene nonylphenyl ether: | 10 parts by weight |
| Quartz: | 50 parts by weight |
| (Catalyst Paste) | |
| Dimethyl polysiloxane terminated by dimethylvinylsiloxy groups at the both ends of the molecular chain: | 100 parts by weight |
| Silicone oil solution containing 0.4% by weight of 1,3-divinyltetramethyl disiloxane-platinum complex: | 3 parts by weight |
| Methylphenyl polysiloxane (phenyl group content: 25 mole %): | 100 parts by weight |
| Quartz: | 100 parts by weight |

Equal amounts of the base paste and catalyst paste were taken and kneaded for 30 seconds by means of a spatula, and the same tests as in Example 1 were carried out. The results obtained are summarized in Table 1.

As shown in Table 1, with respect to the composition of Comparative Example 1, though the permanent deformation was small, the strain in compression was small, and the set material was hard. Also, the tear strength was so low that the set material was confirmed to readily come off.

COMPARATIVE EXAMPLE 2

A base paste and a catalyst paste each having the following composition but not containing the component (G) as in the present invention were prepared.

| | |
|---|---|
| (Base Paste) | |
| Dimethyl polysiloxane terminated by dimethylvinylsiloxy groups at the both ends of the molecular chain: | 100 parts by weight |
| Linear methylhydrogen polysiloxane containing 40 mole % of a methylhydrogen siloxane unit: | 3 parts by weight |
| Polyoxyethylene nonylphenyl ether: | 10 parts by weight |
| Quartz: | 50 parts by weight |
| (Catalyst Paste) | |
| Dimethyl polysiloxane terminated by dimethylvinylsiloxy groups at the both ends of the molecular chain: | 100 parts by weight |
| Silicone oil solution containing 0.4% by weight of 1,3-divinyltetramethyl disiloxane-platinum complex: | 3 parts by weight |
| Hydrophobic fine silica powder having a BET specific surface area of 100 m²/g, whose surface is terminated by $(CH_3)_2SiO_{2/2}$ unit: | 50 parts by weight |

Equal amounts of the base paste and catalyst paste were taken and kneaded for 30 seconds by means of a spatula, and the same tests as in Example 1 were carried out. The results obtained are summarized in Table 1.

As shown in Table 1, with respect to the composition of Comparative Example 2, though the permanent deformation was small, the strain in compression was small, and the set material was hard. Also, the contact angle to water was larger than that in the compositions of Examples 1 to 3 and hence, it was confirmed that the wettability against water was inferior.

TABLE 1

|  | Example 1 | Example 2 | Example 3 | Comparative Example 1 | Comparative Example 2 |
|---|---|---|---|---|---|
| Strain in Compression (%) | 19.5 | 10.3 | 16.2 | 5.5 | 5.2 |
| Permanent deformation (%) | 0.3 | 0.3 | 0.3 | 0.3 | 0.3 |
| Tear strength (N/m) | 8.9 | 8.2 | 9.5 | 4.5 | 8.1 |
| Contact angel (°) | 35 | 40 | 28 | 56 | 60 |

As described above in detail, though the dental impression silicone composition according to the present invention is large in the strain in compression, it is small in the permanent deformation and even after setting, and is still soft. Therefore, upon removing out the impression from the oral cavity of a patient, the impression can be readily removed without giving the patient pain. Also, upon removing out the impression, there are no fears of deformation and coming off. Furthermore, upon pouring a model material such as gypsum into the obtained impression and then removing out the model material, the composition of the invention has such an effect that the model material can be readily removed out.

In addition, the dental impression silicone composition according to the present invention is so superior in the wettability against water that a detail impression in the oral cavity can be preciously taken. Thus, the composition of the invention has such an effect that complicated impressions can be surely taken without failure.

In the light of the above, in accordance with the dental impression silicone composition of the present invention, it has been successful in developing dental impression materials having superior properties which are able to overcome the defects of the conventionally used dental impression materials. Therefore, the invention is quite useful for dentists, and patients and dental technicians and is extremely valuable for contributing to the dental field.

While the invention has been described in detail and with reference to specific embodiments thereof, it will be apparent to one skilled in the art that various changes and modifications can be made therein without departing from the spirit and scope thereof.

What is claimed is:

1. A dental impression silicone composition comprising:
   (A) 100 parts by weight of an organopolysiloxane having at least two aliphatic unsaturated hydrocarbons in one molecule;
   (B) from 0.1 to 30 parts by weight of an organhydrogen polysiloxane having at least three hydrogen atoms directly bonded to the silicon atom in one molecule;
   (C) from 10 to 500 ppm, based on the total amount of the components (A) and (B), of a silicone-soluble platinum compound;
   (D) from 10 to 500 parts by weight of an inorganic filler;
   (E) from 5 to 50 parts by weight of a fine silica powder having a BET specific surface area of from 50 to 500 $m^2/g$, whose surface is made hydrophobic;
   (F) from 0.5 to 50 parts by weight of a nonionic surfactant; and
   (G) from 10 to 200 parts by weight of a methylphenyl polysiloxane of the formula

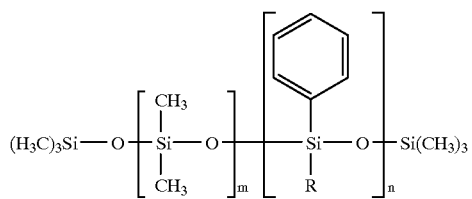

wherein in the formula, R represents a methyl group or a phenyl group; and m and n each represents an integer, $m \geq 0$, $n \geq 0$.

2. The dental impression silicone composition according to claim 1, wherein (A) is a linear organopolysiloxane terminated by vinylsilyl groups at both ends of its molecular chain.

3. The dental impression silicone composition according to claim 1, wherein (C) is a chloroplatinate-vinylsiloxane complex.

4. The dental impression silicone composition according to claim 1, wherein (D) is quartz, cristobalite, diatomaceous earth, fused quartz, glass fibers, titanium dioxide or fumed silica.

5. The dental impression silicone composition according to claim 1, wherein (F) is other than a silicone.

6. The dental impression silicone composition according to claim 1, wherein (F) include nonionic surfactants having a combination of a hydrophilic group with an alkyl group as a lipophilic group, or nonionic surfactants having a combination of a hydrophilic group with a fluorocarbon group in which hydrogen atoms in an alkyl group as a lipophilic group are substituted with fluorine atoms.

* * * * *